United States Patent
Krokoszinski et al.

(10) Patent No.: US 6,864,391 B2
(45) Date of Patent: Mar. 8, 2005

(54) METHOD FOR PRODUCING PROPYLENE HYDROFORMYLATION PRODUCTS AND ACRYLIC ACID AND/OR ACROLEIN

(75) Inventors: Roland Krokoszinski, Weisenheim a.Berg (DE); Ulrich Hammon, Mannheim (DE); Kevin Todd, Lake Jackson, TX (US)

(73) Assignee: BASF Aktiengesellschaft, Ludwigshafen (DE)

( * ) Notice: Subject to any disclaimer, the term of this patent is extended or adjusted under 35 U.S.C. 154(b) by 5 days.

(21) Appl. No.: 10/312,362

(22) PCT Filed: Jun. 27, 2001

(86) PCT No.: PCT/EP01/07337

§ 371 (c)(1),
(2), (4) Date: Dec. 26, 2002

(87) PCT Pub. No.: WO02/00587

PCT Pub. Date: Jan. 3, 2002

(65) Prior Publication Data

US 2004/0015011 A1 Jan. 22, 2004

(30) Foreign Application Priority Data

Jun. 28, 2000 (DE) .......................... 100 31 518

(51) Int. Cl.⁷ .......................... C07C 27/10; C07C 51/16; C07C 45/50
(52) U.S. Cl. .................. 562/512.2; 562/531; 562/534; 568/454; 568/476; 568/478
(58) Field of Search .......................... 562/512.2, 531, 562/534; 568/454, 476, 478

(56) References Cited

U.S. PATENT DOCUMENTS

| | | | |
|---|---|---|---|
| 3,736,355 A | 5/1973 | Croci | 260/533 |
| 3,865,873 A | 2/1975 | Oda | 260/530 |
| 4,224,187 A | 9/1980 | Vanderspurt | 252/437 |
| 4,259,211 A | 3/1981 | Krabetz | 252/443 |
| 4,298,763 A | 11/1981 | Engelbach et al. | 568/479 |
| 5,264,625 A * | 11/1993 | Hammon et al. | 562/532 |
| 5,705,684 A | 1/1998 | Hefner et al. | 562/545 |
| 5,739,391 A * | 4/1998 | Ruppel et al. | 562/532 |
| 2003/0153791 A1 | 8/2003 | Richter et al. | 568/429 |
| 2003/0176743 A1 | 9/2003 | Walz et al. | 568/451 |
| 2004/0024259 A1 | 2/2004 | Richter et al. | 568/451 |

FOREIGN PATENT DOCUMENTS

| | | | | |
|---|---|---|---|---|
| EP | 227 146 | 8/1984 | | |
| EP | 253 409 | 1/1988 | | |
| EP | 257 565 | 3/1988 | | |
| EP | 293 224 | 11/1988 | | |
| EP | 648 730 | 4/1995 | | |
| FR | 150986 | 11/1920 | | |
| GB | 2055367 | * | 3/1981 | C07C/47/02 |

OTHER PUBLICATIONS

Stern et al. Reaction Network and Kinetics of Propane Oxydehydrogenation over Nickel Cobalt Molybdate. Journal of Catalysis, vol. 167 (2), 1997, p 560–569.*

* cited by examiner

*Primary Examiner*—Johann Richter
*Assistant Examiner*—Sikarl A. Witherspoon
(74) *Attorney, Agent, or Firm*—Keil & Weinkauf

(57) ABSTRACT

A process for preparing hydroformylation products of propylene and for preparing acrylic acid and/or acrolein comprises a) feeding a propylene-containing feed in which from 2 to 40% by weight of propane is present and also carbon monoxide and hydrogen into a reaction zone and reacting this mixture in the presence of a hydroformylation catalyst to form hydroformylation products of propane, b) separating a stream consisting essentially of unreacted propylene and propane from the output from the reaction zone, and c) subjecting the stream consisting essentially of propylene and propane to a catalytic gas-phase oxidation in the presence of molecular oxygen to form acrylic acid and/or acrolein.

10 Claims, No Drawings

METHOD FOR PRODUCING PROPYLENE HYDROFORMYLATION PRODUCTS AND ACRYLIC ACID AND/OR ACROLEIN

The present invention relates to a process for preparing hydroformylation products of propylene and for preparing acrylic acid and/or acrolein.

The hydroformylation of propylene is an important industrial process for preparing hydroformylation products of propylene, i.e. butyraldehyde and/or butanol.

The hydroformylation of propylene is carried out industrially in a continuous process in which propylene together with carbon monoxide and hydrogen is fed into a hydroformylation reactor and reacted in the presence of a hydroformylation catalyst. The output from the reactor comprises the hydroformylation products of propylene and also generally significant amounts of unreacted propylene which has to be separated off and, generally together with fresh carbon monoxide and hydrogen, recirculated to the hydroformylation reactor. However, the propane which is present as impurity in the feed propylene or formed by secondary reactions in the hydroformylation reactor and is not capable of hydroformylation is also returned to the reactor together with the recirculated propylene. To prevent the propane concentration in the hydroformylation reactor from rising continually and reaching values at which the hydroformylation reaction ceases, a substream of the recirculated propylene-containing stream has to be continually bled off from the process in order to remove the propane introduced with the propylene feed or formed by secondary reactions from the system.

Not only propane but also unreacted propylene is removed from the system by means of the bleed stream and is thus lost to the further reaction. To keep these losses small, a propylene feed of high purity is generally used. The hydroformylation is usually carried out using a propylene feed having a purity of about 99.5%, with the remainder consisting essentially of propane. This grade of propylene is referred to as "polymer grade propylene". Such a propylene feed of high purity is, however, costly to obtain and is therefore marketed at significantly higher prices than propylene of lower purity. Thus, for example, "chemical grade propylene" containing from about 3 to 7% by weight of propane is significantly cheaper than the abovementioned "polymer grade propylene".

For the reasons mentioned above, a propylene feed having a relatively high proportion of propane cannot be used in an industrial hydroformylation process without appropriate measures being taken. To prevent the propane concentration in the hydroformylation reactor reaching such high values that the hydroformylation reaction ceases, the bleed stream and the accompanying loss of unreacted propylene would have to be made so large that the savings due to the cheaper feedstock would be canceled out.

Separating the stream separated from the hydroformylation product into a propylene-enriched fraction and a propylene-depleted fraction and recirculating only the propylene-enriched fraction to the reaction zone has already been proposed. However, the separation of propylene and propane is difficult because of their similar physical properties. Thus, EP-A-0648730 discloses a process for preparing an oxo product obtained from propylene in which a gas stream separated from the product stream from a propylene hydroformylation is subjected to selective adsorption of the propylene on an adsorbent and subsequent desorption. The alternating adsorption and desorption cycles require periodic pressure and/or temperature changes. The apparatuses required for this are complicated and susceptible to malfunctions.

Acrylic acid is an important basic chemical. Owing to its reactive double bond, it is particularly suitable as a monomer for preparing polymers. Of the acrylic acid produced, the major proportion is esterified prior to polymerization, e.g. to produce adhesives, dispersions or surface coatings. Part of the acrylic acid produced is polymerized directly, e.g. to produce "superabsorbents". It is known that acrylic acid can be prepared by heterogeneously catalyzed gas-phase oxidation of propylene by molecular oxygen over solid catalysts, cf., for example, DE-A-1962431, DE-A-2943707, DE-C-1205502, DE-A-19508558, EP-A-0257565, EP-A-0253409, DE-A-2251364, EP-A-0117146, GB-B-150986 and EP-A-0293224.

Coupling of the preparation of acrylic acid and/or acrolein and the preparation of hydroformylation products of propylene has not been described or suggested in the prior art.

It is an object of the present invention to provide a process for preparing hydroformylation products of propylene which allows the use of propylene feeds in which a proportion of propane is present and permits virtually complete utilization of the propylene and/or propane fed in.

We have found that this object is achieved by using a stream which has been separated off from the reactor output from the hydroformylation of propylene and consists essentially of unreacted propylene and propane as starting material for the preparation of acrylic acid and/or acrolein by catalytic gas-phase oxidation.

The present invention accordingly provides a process for preparing hydroformylation products of propylene and for preparing acrylic acid and/or acrolein, which comprises a) feeding a propylene-containing feed and also carbon monoxide and hydrogen into a reaction zone and reacting this mixture in the presence of a hydroformylation catalyst to form hydroformylation products of propene, b) separating a stream consisting essentially of unreacted propylene and propane from the output from the reaction zone, c) subjecting the stream consisting essentially of propylene and propane to a catalytic gas-phase oxidation in the presence of molecular oxygen to form acrylic acid and/or acrolein.

We have found that the specific impurities which may be present in the propylene/propane stream separated off from the reactor output from the hydroformylation, e.g. carbon monoxide, hydrogen, butyraldehyde, butanol, etc., do not adversely affect the activity, selectivity and operating life of the heterogeneous catalysts used in the gas-phase oxidation of propylene to acrylic acid and/or acrolein and do not interfere in the work-up of the reaction products obtained in this way.

Suitable pressure-rated reaction apparatuses for carrying out the hydroformylation are known to those skilled in the art. They include the generally customary reactors for gas-liquid reactions, e.g. stirred vessels, gas recycle reactors, bubble columns, etc., which may be further divided by means of internals.

The propylene feed which is suitable as starting material for the process of the present invention may comprise a proportion of propane in addition to propylene. It contains, for example, from 0.5 to 40% by weight, preferably from 2 to 30% by weight and in particular from 3 to 10% by weight, of propane. A preferred example is "chemical grade propylene" which contains from 3 to 10% by weight of propane. It is obtained, for example, by reaction of naphtha or natural gas in a steam cracker and subsequent work-up by distillation. A further example of a suitable propylene feed is "refinery grade propylene" which has propane contents of from 20 to 30%.

Carbon monoxide and hydrogen are usually used in the form of a mixture, namely synthesis gas. The composition of the synthesis gas used in the process of the present invention can vary within a wide range. The molar ratio of carbon monoxide to hydrogen is generally from 5:1 to 1:5, preferably from 2:1 to 1:2, in particular about 45:55.

The temperature in the hydroformylation reaction is generally in a range from 50 to 200° C., preferably from about 60 to 190° C., in articular from about 90 to 190° C. The reaction is preferably carried out at a pressure in the range from about 10 to 700 bar, more preferably from 15 to 200 bar, in particular from 15 to 60 bar. The reaction pressure can be varied as a function of the activity of the hydroformylation catalyst used.

Suitable hydroformylation catalysts are the customary transition metal compounds and complexes which are known to those skilled in the art and can be used both with or without cocatalysts. The transition metal is preferably a metal of transition group VIII of the Periodic Table, in particular Co, Ru, Rh, Pd, Pt, Os or Ir, especially Rh, Co, Ir or Ru. Particularly preferred hydroformylation catalysts for the hydroformylation of propylene are phosphorus-containing rhodium catalysts such as $RhH(CO)_2(PPh_3)_2$ or $RhH(CO)(PPh_3)_3$. Suitable hydroformylation catalysts are described, for example, in Beller et al., Journal of Molecular Catalysis A, 104 (1995), pp. 17–85, which is hereby fully incorporated by reference.

The prior art provides a number of industrial processes for obtaining a stream comprising propylene and propane whose use is, in general, not critical to the success of the process of the present invention as long as certain preconditions have been met. Therefore, the output from the reaction zone can be subjected to a single-stage or multistage separation operation to give at least a stream comprising the major part of the hydroformylation product, i.e. butyraldehyde and/or butanol, and a stream consisting essentially of unreacted propylene and propane. Depending on factors such as the type of discharge process, the purity of the synthesis gas used, etc., further streams may be obtained, for example waste gases comprising synthesis gas, high-boiling by-products of the hydroformylation and/or streams comprising hydroformylation catalyst, and these are, with or without work-up, recirculated wholly or partly to the reaction zone or discharged from the process. For example, the hydroformylation product and any components having boiling points higher than that of the hydroformylation product can firstly be separated off from the output from the reaction zone. A mixture of unreacted propylene and propane can subsequently be condensed out, e.g. by cooling.

However, the stream consisting essentially of unreacted propylene and propane is advantageously obtained by firstly separating a crude hydroformylation product in which unreacted propylene and propane are present in dissolved form from the output from the reaction zone, e.g. in a gas/liquid separator, if appropriate after prior depressurization of the output to a pressure lower than that prevailing in the reactor, and then subjecting the crude hydroformylation product to a degassing step which produces a stream consisting essentially of unreacted propylene and propane. The rest of the reactor output which has been separated from the crude hydroformylation product and which generally comprises unreacted synthesis gas, inert gas (e.g. methane, $N_2$, $CO_2$) and some of the unreacted propylene present in the reactor output and some of the propane is generally recirculated wholly or partly to the reaction zone.

For degassing the dissolved propylene and propane, the crude hydroformylation product can be further depressurized, heated and/or treated with a stripping gas, for example synthesis gas. Degassing is advantageously carried out in a column where the crude hydroformylation product is introduced in the region of the middle of the column and the degassed hydroformylation product is taken off at the bottom of the column and can be passed to further work-up, and a liquid or gaseous stream consisting essentially of unreacted propylene and propane is taken off at the top of the column.

The degassing of the crude hydroformylation product is advantageously carried out in a column at generally from 4 to 12 bar, preferably from 6 to 10 bar and particularly preferably from 6 to 8 bar, with the temperature in the bottom of the column being maintained in a range of generally from 120 to 190° C., preferably from 140 to 170° C. and particularly preferably from 140 to 160° C., depending on the pressure employed. As separation internals, it is possible to use, for example, ordered packing, random packing or trays in the degassing column; preference is given to using ordered packing. The number of theoretical plates in the degassing column is generally in the range from 8 to 40, preferably in the range from 10 to 25 and particularly preferably in the range from 10 to 20. The degassing column is advantageously operated so that the butyraldehyde content in the propylene- and propane-containing stream obtained therefrom does not exceed 0.5% by weight, preferably 0.1% by weight and particularly preferably 0.01% by weight. The precise operating conditions for the degassing column can be calculated in a routine fashion by a person skilled in the art as a function of the separation performance of the column used by means of conventional calculation methods on the basis of the known vapor pressures and vaporization equilibria of the components present in the crude hydroformylation product.

It can be advantageous to use two degassing columns which are operated under different conditions in place of a single degassing column. In this embodiment, the first degassing column is generally operated at a lower pressure than the second degassing column. For example, the first column can be operated under the above-described pressure and temperature conditions and the second column can be operated at a pressure of generally from 6 to 30 bar, preferably from 10 to 26 bar, and temperatures of generally from 140 to 200° C. This procedure enables degassing to be carried out in a particularly gentle manner in the first column, while better separation, for example of butyraldehydes, is achieved in the degassing at higher pressure in the second column.

Depending on the type of catalyst used in the gas-phase oxidation to form acrolein and/or acrylic acid, it can also be advantageous to adjust the water content of the stream comprising propylene and propane obtained from the degassing column so that it does not exceed 50 ppm. This measure is particularly advantageous when the stream comprising propene and propane is fed in liquid form to the acrolein and/or acrylic acid plant. This can be achieved by, for example, installing a phase separator in the runback line at the top of the degassing column so that water (formed by condensation of the aldehydes to form high-boiling by-products) which is distilled off azeotropically with propylene and propane is separated off from the propylene/propane mixture returned as runback to the column. As an alternative, the liquid propylene/propane mixture can be passed through a phase separator or, if particularly low water contents are sought, over a desiccant such as molecular sieves 4 Å or molecular sieves 3 Å for the purpose of separating off the water, before it is fed to the gas-phase oxidation. The water content of a gaseous propene/propane stream can, if desired, likewise be reduced by adsorption of the water on a desiccant, e.g. molecular sieves 4 Å or molecular sieves 3 Å.

The above-described measures make it possible to reduce the content of butyraldehydes and, if desired, water in the feed stream to the gas-phase oxidation to form acrolein and/or acrylic acid or, if appropriate, to an oxydehydrogenation stage in which part of the propane is subjected to an oxidizing dehydrogenation to propylene and the stream comprising propylene and propane is enriched in propylene preceding this gas-phase oxidation to the values indicated above. Phosphorus-containing compounds (e.g. free ligand from the hydroformylation) can generally not be detected in the propylene/propane stream obtained from the degassing column under the conditions mentioned.

The crude hydroformylation product in which unreacted propylene and propane are present in dissolved form can be separated from the output from the reaction zone in various ways. It is possible to use, for example, a liquid output process in which the output which is essentially liquid except for the synthesis gas used in excess for the hydroformylation is depressurized from the reaction zone and if, as a result of the pressure decrease, separated into a liquid phase consisting essentially of high-boiling by-products, the homogeneously dissolved hydroformylation catalyst and part of the hydroformylation product and dissolved, unreacted propylene and propane, and a gas phase consisting essentially of hydroformylation product, unreacted propylene and propane and unreacted carbon monoxide and hydrogen and inert gases (e.g. $N_2$, $CO_2$, methane). The liquid phase can be recirculated to the reactor as a recycled stream, possibly after further separation of the product aldehydes contained therein. The crude hydroformylation product is obtained by at least partial condensation of the gas phase. The gas phase remaining after the condensation is recirculated wholly or partly to the reaction zone.

The gas and liquid phases initially obtained in the depressurization step can advantageously be worked up by the method described in WO 97/07086. For this purpose, the liquid phase is heated and introduced into the upper region of a column, while the gas phase is introduced at the bottom of the column. In this way, liquid phase and gas phase pass through the column in countercurrent. To increase contact of the phases with one another, the column is preferably provided with packing. As a result of the intimate contact of the gas phase with the liquid phase, the residual amounts of hydroformylation product, unreacted propylene and propane present in the liquid phase are transferred to the gas phase, so that the gas stream leaving the top of the column is enriched in hydroformylation product, unreacted propylene and propane compared to the gas stream introduced at the lower end of the column. Further work-up of the gas stream leaving the column and of the liquid phase leaving the column is carried out as described above, for example in a degassing column.

As an alternative, it is possible to employ the gas recycle process in which a gas stream is taken from the gas space of the hydroformylation reactor. This gas stream consists essentially of synthesis gas, unreacted propylene and propane together with an amount depending on the vapor pressure in the hydroformylation reactor of the hydroformylation product formed in the hydroformylation reaction. The crude hydroformylation product present in the gas stream is condensed out, e.g. by cooling, and the gas stream which has been freed of the liquid fraction is recirculated to the hydroformylation reactor. The unreacted propylene and propane present in solution in the condensed, crude hydroformylation product can then be liberated as described, e.g. in a degassing column.

The stream consisting essentially of unreacted propylene and propane comprises, for example, from 40 to 80% by weight, preferably from 60 to 80% by weight, of propylene and from 20 to 60% by weight, preferably from 20 to 40% by weight, of propane.

Merely by way of example, a typical composition, including impurities, of a stream comprising unreacted propylene and propane, as can be liberated in the degassing step by means of two degassing columns and subsequent drying by means of molecular sieves 3 Å is given below:

| | |
|---|---|
| propylene | 68% by weight |
| propane | 30% by weight |
| methane | 1.7% by weight |
| carbon monoxide | 0.28% by weight |
| carbon dioxide | 0.38% by weight |
| ethane | 0.20% by weight |
| hydrogen | 350 ppm by weight |
| butyraldehyde | 10 ppm by weight |
| water | 5 ppm by weight. |

The gaseous stream consisting essentially of unreacted propylene and propane is subjected to a catalytic gas-phase oxidation by methods known per se to prepare acrylic acid and/or acrolein. The stream can of course be mixed with propylene-containing feeds from other sources, e.g. a steam cracker, to form a feed for the gas-phase oxidation. In this case, it is then possible, for example, to use a mixed propene stream of the following composition for the gas-phase oxidation to form acrolein and/or acrylic acid:

| | |
|---|---|
| propylene: | $\geq$94% by weight |
| propane: | $\leq$6% by weight |
| methane and/or ethane: | $\leq$4000 ppm by weight |
| $C_4$-hydrocarbons: | $\leq$5 ppm by weight |
| acetylene: | $\leq$1 ppm by weight |
| water: | $\leq$5 ppm by weight |
| hydrogen: | $\leq$100 ppm by weight |
| oxygen: | $\leq$2 ppm by weight |
| sulfur-containing compounds: (calculated as sulfur) | $\leq$2 ppm by weight |
| chlorine-containing compounds: (calculated as chlorine) | $\leq$1 ppm by weight |
| $CO_2$: | $\leq$1000 ppm by weight |
| CO: | $\leq$700 ppm by weight |
| cyclopropane: | $\leq$10 ppm by weight |
| propadiene and/or propyne: | $\leq$5 ppm by weight |
| hydrocarbons > C5 (green oils): | $\leq$10 ppm by weight |
| compounds containing carbonyl groups (calculated as $Ni(CO)_4$: | $\leq$10 ppm by weight |
| butyraldehyde: | $\leq$2.5 ppm by weight |
| P- and/or As-containing compounds: | not detectable |

The feed, which may be mixed with an inert diluent gas, is passed in admixture with oxygen over a heterogeneous catalyst, generally a mixed oxide catalyst comprising transition metals, e.g. molybdenum, vanadium, tungsten and/or iron, at elevated temperatures, usually from 200 to 450° C., and atmospheric or superatmospheric pressure so as to convert it into acrylic acid and/or acrolein by oxidation. On the subject, reference may be made, for example, to DE-A-4405059, EP-A-0253409, EP-A-0092097 and DE-A-4431949. The conversion into acrylic acid can be carried out in one or two stages. In the two-stage method, the propylene is oxidized to acrolein in a first stage and the acrolein is oxidized to acrylic acid in a second stage. Heterogeneous catalysts which are preferred for the first stage are oxidic multicomponent catalysts based on oxides of molybdenum, bismuth and iron, while corresponding catalysts based on oxides of molybdenum and vanadium are preferred in the second stage.

The propane can serve as diluent gas and/or starting material in the gas-phase oxidation. A suitable process in which propane as starting material is converted directly into acrylic acid is described in EP-B-0608838. Alternatively, the propylene/propane stream obtained in the hydroformylation can, before being used in the production of acrylic acid, be subjected to a catalytic oxydehydrogenation as described, for example, in Catalysis Today, 24 (1995), 307–313, or U.S. Pat. No. 5,510,558, a homogeneous oxydehydrogenation or a catalytic dehydrogenation as described in DE-A-19508558, EP-A-0293224 or EP-A-0117146 to increase the proportion of propylene in the stream.

The reaction of propylene to form acrylic acid and/or acrolein is strongly exothermic. The propylene/propane stream is therefore advantageously diluted with an inert diluent gas, e.g. atmospheric nitrogen, carbon dioxide, methane and/or steam. Although the type of reactors used is subject to no restriction, it is advantageous to use shell-and-tube heat exchangers charged with the oxidation catalyst, since these allow the major part of the heat liberated in the reaction to be removed by thermal conduction, convection and radiation to the cooled reactor walls.

The single or two-stage catalytic gas-phase oxidation to acrylic acid does not give pure acrylic acid, but rather a gaseous mixture which may comprise not only acrylic acid but also, as secondary components, mainly unreacted acrolein and/or propylene, propane, water vapor, carbon monoxide, carbon dioxide, nitrogen, oxygen, acetic acid, propionic acid, formaldehyde, further aldehydes and maleic anhydride.

The acrylic acid can be separated from the resulting reaction gases by, for example, countercurrent absorption using a high-boiling inert solvent such as diphenyl ether, biphenyl and/or dimethyl phthalate or the like, cf. DE 2136396 and DE-A-4308087, and then be isolated, for example by distillation.

Alternatively, it is possible to subject the reaction product obtained in the gas-phase oxidation to a condensation, in particular a partial or total condensation, and to separate the acrylic acid from the resulting solution by crystallization. The condensation is preferably carried out in a column. Here, the column is provided with separation-active internals, in particular ordered packing, random packing and/or trays, preferably bubblecap trays, sieve trays, valve trays and/or dual-flow trays. On passage through the column, the condensible components of the gaseous product mixture from the gas-phase oxidation are fractionally condensed by cooling. Since, as a result of impurities and diluent gases which may be used, the gas mixture generally comprises a high-boiling fraction, an intermediate-boiling fraction and a low-boiling fraction and also uncondensable components, one or more side offtakes can be provided at appropriate places on the column. The condensation in the column thus allows fractionation into the individual components. Suitable columns include at least one cooling apparatus, for which all customary heat exchangers are suitable, in which the heat liberated in the condensation is removed indirectly. Preference is given to shell-and-tube heat exchangers, plate heat exchangers and air coolers. Suitable cooling media are, for example, air and cooling liquids, in particular water. The pressure prevailing in the column depends on the amount of uncondensable components and is preferably from 0.5 to 5 bar absolute, in particular from 0.8 to 3 bar absolute. The precise operating conditions for the column, for example temperature and pressure, connection and arrangement of the cooling apparatus(es) can be determined as a function of the composition of the mixture by a person skilled in the art by means of customary optimization. In a preferred embodiment, the hot gas mixture is cooled directly or indirectly prior to condensation. In the case of direct cooling, the cooling medium used is preferably the high-boiling fraction obtained in the fractional condensation. As an alternative, it is possible to use a cooling medium which is not inherent in the system, for example diphenyl ether, biphenyl and/or dimethyl phthalate. Precooling can be integrated into the bottom region of the column or can be carried out separately from the column in a suitable apparatus, e.g. a gas cooler, a quench or a flash vessel.

The solution obtained in the condensation, which comprises acrylic acid, can subsequently be crystallized. Crystallization can be carried out continuously or batchwise, in one or more stages. It is preferably carried out in one stage. The resulting crystals of acrylic acid are subsequently separated from the mother liquor. The mother liquor is advantageously recirculated at least partly to the condensation of the gaseous product mixture. A particularly preferred process for preparing acrylic acid is described in DE 197 40 252, which is hereby fully incorporated by reference.

The offgas leaving the gas-phase oxidation to form acrolein and/or acrylic acid, which, depending on the oxidation process employed, comprises unreacted propane as significant component of value, can be utilized, for example, as cracker feed or as raw material for a propane oxydehydrogenation plant or else can be used as fuel for generation of steam or energy recovery.

The integrated butyraldehyde and acrylic acid production achieved by means of the process of the present invention makes it possible for the propylene raw material fed to the hydroformylation plant to be optimally utilized at minimum cost and thus improves the economics of both processes. It was hitherto necessary, in order to make virtually full use of the propylene fed to the hydroformylation plant if the valuable propylene present in the offgas from the hydroformylation plant was not to be used simply but unprofitably as fuel, to separate the unreacted propylene from the propane present in an expensive-to-operate propene/propane separation plant before being recirculated to the hydroformylation reactor. The use of the propene- and propane-containing offgas from the hydroformylation plant as raw material for a steam cracker, should this be available at the site concerned, is also less economically advantageous than the process of the present invention, since no additional added value is created in respect of the propylene present in this cracker feed. Another way of achieving virtually complete utilization of the olefin raw material fed to a hydroformylation plant is proposed in EP-A 188246, namely the utilization of the propylene- and propane-containing offgas from a first hydroformylation reactor as raw material for a second hydroformylation reactor which is decoupled from the first. However, this solution, too, results in significant additional capital costs for the second, decoupled reactor and naturally also additional operating costs. In contrast, the process of the present invention allows optimal utilization of the propylene raw material fed to the hydroformylation plant virtually without appreciable additional capital costs, since it is generally necessary to install only a supply line between the hydroformylation plant and the acrylic acid plant and virtually no appreciable, additional operating costs are incurred in operating the degassing column according to the present invention for separating off a propylene/propane stream suitable for acrolein/acrylic acid production.

The success of the process of the present invention is surprising since a person skilled in the art would have feared that the use of the offgas stream comprising propylene and propane from a hydroformylation plant as raw material for the preparation of acrylic acid would have adverse effects on the purity of the acrylic acid produced therefrom and would accordingly restrict its possible uses and marketing opportunities.

The invention is illustrated by the following example.

EXAMPLE

A feed stream of 1 kg/h of "chemical grade propylene" having a propylene content of 95% by weight and a propane content of 5% by weight together with the synthesis gas necessary for the reaction was fed into a hydroformylation reactor. The product formed, namely a mixture of n-butyraldehyde and isobutyraldehyde, together with unreacted propylene and the propylene introduced and formed was discharged from the reactor with the aid of a circulating gas stream. The condensable components were condensed in a downstream cooler and collected in a subsequent separator. The condensate comprised 78.3% by weight of butyraldehyde, 14.3% by weight of propylene and 7.4% by weight of propane. This mixture was fed to a degassing column (2.03 kg/h) where it was separated into a $C_3$-free aldehyde stream (the crude oxo product) at the bottom (1.6 kg/h) and a mixture of 66% by weight of propylene and 34% by weight of propane at the top (0.44 kg/h).

The stream obtained at the top was combined with the feed to the synthesis stage of an acrylic acid plant (0.33 kg/h of "chemical grade propylene"). The feed accordingly had a composition of 78.4% by weight of propylene and 21.6% by weight of propane.

The feed stream was vaporized and passed together with air and nitrogen through a steel tube which contained an oxidation catalyst 2 based on Mo and prepared in accordance with Example 1c), 1 from U.S. Pat. No. 4,298,763, and was maintained at about 340° C. Reaction with oxygen in the tube gave an acrolein yield of 87.4 mol % and an acrylic acid yield of 1 mol % at a propylene conversion of 95.3 mol %.

In a second experiment, the acrolein product mixture obtained above was, without further work-up, passed through a second steel tube of the same design which was charged with a catalyst for the oxidation of acrolein to acrylic acid prepared as described in Example 1 of U.S. Pat. No. 4,259,211. Before the acrolein product mixture from the first steel tube entered the second steel tube, air was added to it in such an amount that the oxygen content of the reaction mixture leaving the second steel tube was 3.2% by volume. At a temperature of 291° C. in the second steel tube (reactor), an acrylic acid yield of 92.2%, based on the acrolein used, was achieved at an acrolein conversion of 99.3%.

We claim:

1. A process for preparing hydroformylation products of propylene and for preparing acrylic acid and/or acrolein, which comprises a) feeding a propylene-containing feed and also carbon monoxide and hydrogen into a reaction zone and reacting this mixture in the presence of a hydroformylation catalyst to form hydroformylation products of propene, b) separating a stream consisting essentially of unreacted propylene and propane from the output from the reaction zone, c) subjecting the stream consisting essentially of propylene and propane to a catalytic gas-phase oxidation in the presence of molecular oxygen to form acrylic acid and/or acrolein.

2. A process as claimed in claim 1, wherein the propylene-containing feed contains from 2 to 40% by weight of propane.

3. A process as claimed in claim 1, wherein the stream consisting essentially of unreacted propylene and propane is obtained by firstly separating a crude hydroformylation product in which unreacted propylene and propane are present in dissolved form from the output from the reaction zone and subjecting the crude hydroformylation product to a degassing step.

4. A process as claimed in claim 3, wherein the output from the reaction zone is essentially gaseous and the crude hydroformylation product is separated off by partial condensation of the gaseous output.

5. A process as claimed in claim 3, wherein the output from the reaction zone is essentially liquid, the liquid output is depressurized, resulting in separation into a liquid phase consisting essentially of high-boiling by-products, the homogeneously dissolved hydroformylation catalyst and small amounts of hydroformylation product, small amounts of unreacted propylene and small amounts of propane and a gas phase consisting essentially of hydroformylation product, unreacted propylene and propane and unreacted carbon monoxide and hydrogen, and the crude hydroformylation product is obtained by at least partial condensation of the gas phase.

6. A process as claimed in claim 3, wherein two degassing columns are used for the degassing step to which the crude hydroformylation product is subjected.

7. A process as claimed in claim 1, wherein the hydroformylation catalyst used is a phosphorus-containing rhodium catalyst.

8. A process as claimed in claim 1, wherein the stream consisting essentially of unreacted propylene and propane is mixed with an inert diluent gas and brought into contact with a heterogeneous catalyst in the presence of oxygen in at least one oxidation zone.

9. A process as claimed in claim 8, wherein the stream consisting essentially of unreacted propylene and propane is brought into contact with a first heterogeneous catalyst in a first oxidation zone to give an acrolein-containing intermediate product gas mixture and the intermediate product gas mixture is brought into contact with a second heterogeneous catalyst in a second oxidation zone to give a product gas mixture comprising acrylic acid.

10. A process as claimed in claim 1, wherein the stream consisting essentially of unreacted propylene and propane is subjected to an oxydehydrogenation to increase its propylene content before it is subjected to catalytic gas-phase oxidation to form acrylic acid and/or acrolein.

* * * * *